US010350197B2

(12) United States Patent
Springman et al.

(10) Patent No.: US 10,350,197 B2
(45) Date of Patent: Jul. 16, 2019

(54) METHODS OF INHIBITING LEUKOTRIENE A4 HYDROLASE

(71) Applicant: Celtaxsys, Inc., Atlanta, GA (US)

(72) Inventors: Eric B. Springman, Atlanta, GA (US); Margaret McCrann Pugh, Atlanta, GA (US); Lopa Bhatt, Roswell, GA (US); Ralph Grosswald, Alpharetta, GA (US)

(73) Assignee: Celtaxsys, Inc., Atlanta, GA (US)

( * ) Notice: Subject to any disclaimer, the term of this patent is extended or adjusted under 35 U.S.C. 154(b) by 0 days.

(21) Appl. No.: 15/801,482

(22) Filed: Nov. 2, 2017

(65) Prior Publication Data

US 2018/0117014 A1 May 3, 2018

Related U.S. Application Data

(63) Continuation of application No. 14/850,061, filed on Sep. 10, 2015, now Pat. No. 9,820,974, which is a continuation of application No. PCT/US2014/023138, filed on Mar. 11, 2014.

(60) Provisional application No. 61/776,981, filed on Mar. 12, 2013.

(51) Int. Cl.
A61K 31/422 (2006.01)
A61K 45/06 (2006.01)
A61K 31/4995 (2006.01)
A61K 9/16 (2006.01)

(52) U.S. Cl.
CPC ............. A61K 31/422 (2013.01); A61K 9/16 (2013.01); A61K 31/4995 (2013.01); A61K 45/06 (2013.01)

(58) Field of Classification Search
CPC .................................................. A61K 31/422
See application file for complete search history.

(56) References Cited

U.S. PATENT DOCUMENTS

| 3,929,765 | A | 12/1975 | Suzuki |
| 4,576,943 | A | 3/1986 | Tomcufcik et al. |
| 4,582,833 | A | 4/1986 | Tomcufcik et al. |
| 5,308,852 | A | 5/1994 | Girard et al. |
| 5,723,492 | A | 3/1998 | Chandrakumar et al. |
| 5,952,349 | A | 9/1999 | Asberom et al. |
| 6,309,561 | B1 | 10/2001 | Hasegawa et al. |
| 6,348,487 | B1 | 2/2002 | Connor et al. |
| 6,372,736 | B1 | 4/2002 | Kemp et al. |
| 6,380,203 | B1 | 4/2002 | Bilodeau et al. |
| 6,407,140 | B1 | 6/2002 | Gregory et al. |
| 6,451,798 | B2 | 9/2002 | Varkhedkar et al. |
| 6,534,521 | B2 | 3/2003 | Connor et al. |
| 6,552,023 | B2 | 4/2003 | Zablocki et al. |
| 6,635,644 | B2 | 10/2003 | Salituro et al. |
| 6,699,873 | B1 | 3/2004 | Maguire et al. |
| 6,734,184 | B1 | 5/2004 | Barlaam et al. |
| 6,846,812 | B2 | 1/2005 | Dalko et al. |
| 6,869,975 | B2 | 3/2005 | Abe et al. |
| 6,875,483 | B2 | 4/2005 | Matsuoka et al. |
| 6,924,313 | B1 | 8/2005 | Sikorski et al. |
| 7,169,779 | B2 | 1/2007 | Salituro et al. |
| 7,402,684 | B2 | 7/2008 | Sandanayaka et al. |
| 7,488,741 | B2 | 2/2009 | Lamberty et al. |
| 7,597,897 | B2 | 10/2009 | Capecchi et al. |
| 7,645,779 | B2 | 1/2010 | Abe et al. |
| 7,674,899 | B2 | 3/2010 | Peters et al. |
| 7,718,669 | B2 | 5/2010 | Petry et al. |
| 7,737,145 | B2 * | 6/2010 | Arnaiz .................. C07D 451/02 514/248 |
| 7,816,365 | B2 | 10/2010 | Schiemann et al. |
| 7,820,675 | B2 | 10/2010 | Johansson et al. |
| 7,820,821 | B2 | 10/2010 | Gopalaswamy et al. |
| 7,893,257 | B2 | 2/2011 | Grimm et al. |
| 7,902,181 | B2 | 3/2011 | Furber et al. |
| 7,915,298 | B2 | 3/2011 | Gosselin et al. |
| 7,932,272 | B2 | 4/2011 | Nakamoto et al. |
| 7,935,707 | B2 | 5/2011 | Aebi et al. |
| 8,246,935 | B2 | 8/2012 | Mueller-Walz et al. |
| 8,357,684 | B2 | 1/2013 | Bacani et al. |
| 8,569,303 | B2 * | 10/2013 | Arnaiz .................. C07D 451/02 514/247 |
| 8,609,669 | B2 | 12/2013 | Xu et al. |
| 8,846,655 | B2 | 9/2014 | Decorte et al. |
| 9,006,235 | B2 | 4/2015 | Naidu et al. |
| 9,133,146 | B2 | 9/2015 | Abeywardane et al. |
| 9,315,509 | B2 | 4/2016 | Arnaiz et al. |
| 9,820,974 | B2 * | 11/2017 | Springman ............ A61K 45/06 |
| 9,861,601 | B2 | 1/2018 | Nicolls et al. |
| 2004/0006114 | A1 | 1/2004 | Coleman et al. |
| 2004/0198777 | A1 | 10/2004 | Ghosh et al. |
| 2005/0043378 | A1 | 2/2005 | Axe et al. |
| 2005/0043379 | A1 | 2/2005 | Axe et al. |
| 2005/0113408 | A1 | 5/2005 | Helgadottir et al. |
| 2006/0063784 | A1 | 3/2006 | Wang et al. |
| 2006/0211729 | A1 | 9/2006 | Fyrnys et al. |
| 2006/0223792 | A1 | 10/2006 | Butler et al. |
| 2007/0112006 | A1 | 5/2007 | Schiemann et al. |
| 2007/0155726 | A1 | 7/2007 | Arnaiz et al. |
| 2008/0096906 | A1 | 4/2008 | Galley et al. |
| 2008/0267885 | A1 | 10/2008 | Capecchi et al. |
| 2009/0233922 | A1 | 9/2009 | Zhuo et al. |

(Continued)

FOREIGN PATENT DOCUMENTS

CN 102030700 A 4/2011
CN 103159742 A 6/2013
(Continued)

OTHER PUBLICATIONS

Celli et al. Respiratory Medicine, 2011, vol. 105, pp. 1176-1188 (Year: 2011).*

(Continued)

Primary Examiner — James D. Anderson
(74) Attorney, Agent, or Firm — Elmore Patent Law Group, P.C.; Mahreen Chaudhry-Hoda; Carolyn S. Elmore

(57) ABSTRACT

The present invention is directed to methods of inhibiting $LTA_4$-h in a human patient and method of treating a condition ameliorated by the inhibition of leukotriene $A_4$ hydrolase activity in a human patient comprising administering to said human patient the compound, 4-{5-[4-(4-Oxazol-2-yl-phenoxy)-benzyl]-2,5-diaza-bicyclo[2.2.1]hept-2-ylm-ethyl}-benzoic acid.

8 Claims, 2 Drawing Sheets

(56) References Cited

U.S. PATENT DOCUMENTS

| | | |
|---|---|---|
| 2010/0029619 A1 | 2/2010 | Uchikawa et al. |
| 2010/0029657 A1 | 2/2010 | Levin et al. |
| 2010/0069417 A1 | 3/2010 | Bouaboula et al. |
| 2010/0093668 A1 | 4/2010 | Babin et al. |
| 2010/0099694 A1 | 4/2010 | Babin et al. |
| 2010/0210630 A1* | 8/2010 | Arnaiz ............. C07D 451/02 514/218 |
| 2010/0260859 A1 | 10/2010 | Ruddy et al. |
| 2011/0009429 A1 | 1/2011 | Oakley et al. |
| 2011/0009454 A1 | 1/2011 | Matsuzaki et al. |
| 2011/0105475 A1 | 5/2011 | Roche et al. |
| 2012/0028954 A1 | 2/2012 | Goff et al. |
| 2012/0263680 A1 | 10/2012 | Lander et al. |
| 2012/0302610 A1 | 11/2012 | Chakravarty et al. |
| 2013/0123243 A1 | 5/2013 | Arnaiz et al. |
| 2013/0237499 A1 | 9/2013 | Zheng et al. |
| 2013/0251787 A1 | 9/2013 | Nicolls et al. |
| 2016/0067226 A1 | 3/2016 | Grosswald et al. |
| 2016/0068522 A1 | 3/2016 | Davey et al. |
| 2016/0068524 A1 | 3/2016 | Guilford |
| 2016/0068534 A1 | 3/2016 | Guilford |
| 2016/0272649 A1 | 9/2016 | Kochanny et al. |

FOREIGN PATENT DOCUMENTS

| | | |
|---|---|---|
| EP | 1611902 A1 | 1/2006 |
| GB | 1221006 A | 2/1971 |
| JP | 2001354657 A | 12/2001 |
| JP | 2005008581 A | 1/2005 |
| WO | 02064211 A1 | 8/2002 |
| WO | 02069901 A2 | 9/2002 |
| WO | 02072621 A2 | 9/2002 |
| WO | 03010158 A1 | 2/2003 |
| WO | 02072621 A3 | 5/2003 |
| WO | 03037271 A2 | 5/2003 |
| WO | 02069901 A3 | 10/2003 |
| WO | 2004035746 A2 | 4/2004 |
| WO | 2004089410 A1 | 10/2004 |
| WO | 2004099164 A1 | 11/2004 |
| WO | 2005027886 A2 | 3/2005 |
| WO | 2005027886 A3 | 6/2005 |
| WO | 2005054246 A2 | 6/2005 |
| WO | 2007007069 A1 | 1/2007 |
| WO | 2010011912 A1 | 1/2010 |
| WO | 2010015818 A1 | 2/2010 |
| WO | 2011071758 A1 | 6/2011 |
| WO | 2012125832 A2 | 9/2012 |

OTHER PUBLICATIONS

Grice et al. J. Med. Chem., 2008, vol. 51, pp. 4150-4169 (Year: 2008).*

Online "http://web.archive.org/web/20031225052253/http://www.specs.net/", Dec. 25, 2003, accessed Apr. 1, 2015.

Online "http://web.archive.org/web/20120317091129/http://www.fchgroup.net/" dated Mar. 1, 2012, accessed Oct. 12, 2016.

Online "http://web.archive.org/web/20130122020518/http://www.chembridge.com/screening_libraries/" 2011, accessed Oct. 10, 2015.

Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.

Online: "http://web.archive.org/web/20120301075525/http://www.fchgroup.net/products.php" dated Mar. 1, 2012 accessed Oct. 12, 2016.

STN-Chemical database Registry RN 1322312-60-6 for N-[(3-Phenoxyphenyl)methyl]-6-(1-piperidinyl)-3-Pyridinemethanamine, Entered STN: Aug. 24, 2011.

Inflammation, Wikipedia, 2017, 1.

Pharmaceutical Acceptable Excipients FDA guidelines, 2005, 1-12.

Anonymous, "Celtaxsys Announces Successful Completion of Phase 1 Clinical Trial for Development of CTX-4430—FirstWord Pharma", Retrieved from the Internet: URL:http://www.firstwordpharma.com/node/1139589?tsid=17#axzz4M7ubNn38 [retrieved on Oct. 4, 2016], Sep. 16, 2013.

Arnaiz, D. et al., "Diamine derivatives as inhibitors of leukotriene A4 hydrolase and their preparation, pharmaceutical compositions and use in the treatment of inflammatory disorders", CA147:166353, 2007.

Banker, G. S. et al., Modern Pharmaceutics, 3rd., Marcel Dekker, Inc., NY, 1996, 596.

Beaumont, K. et al., "Design of Ester Prodrugs to Enhance Oral Absorption of Poorly Permeable Compounds: Challenges to the Discovery Scientist", Current Drug Metabolism, 4, 2003, 461-485.

Bhatt, et al., Seminars in Immunology, 33, 2017, 65-73.

Breitenstein, W. et al., "Preparation of substituted pyrrolidines as renin inhibitors", CA145: 103533, 2006.

Bridger, G. J. et al., "Preparation of piperidines as chemokine receptor, particularly CCR5, modulators for treatment of inflammatory and autoimmune diseases", CA143: 97274, 2005.

Brodin, P. et al., "Benzamides, pyridopyrimidines and related compounds as antiinfective compounds and their preparation and use in the treatment of tuberculosis", CA152: 168983, 2010.

Coats, S. J. et al., "4-Substituted 2-phenoxyphenylamines as delta opioid receptor modulators and their preparation and use in the treatment of diseases", CA154: 540153, 2011.

Connors, K. A. "The Stability of Cyclodextrin Complexes in Solution", Chem. Rev., 97, 1997, 1325-1357.

Fieser, L. et al., Reagents for Organic Synthesis, vol. 1, Wiley: NY, Pub Date Discrepancy, 1974, 723-730.

Greene, T. W. et al., Protective Groups in Organic Synthesis, John Wiley & Sons: NY, Pub Date Discrepancy, 1982, 218-220, 224, 251.

Hauptmann, et al., Chem. Rev., 62, 1962, 347-404.

Hutchins, T. O. "Selective Reductive Displacement of Alkyl Halides and Sulfonate Esters with Cyanoborohydride Reagents in Hexamethylphosphoramide", J. Org. Chem., 42(1), 1977, 82-91.

Jantzen, et al., Modern Pharmaceutics, 1996, 596.

Khim, et al., "Discovery of novel and potent aryl diamines as leukotriene A4 hydrolase inhibitors", Bioorg. Med. Chem. Lett., 18(14): Jul. 15, 2008, 3895-3898.

Kurimura, M. et al., "Preparation of N,N-substituted 3-aminopyrrolidine compounds useful as monoamines reuptake inhibitors", CA149: 53863, 2008.

Labaudiniere, R. et al., "w-[(w-Arylalkyl)aryl]alkanoic Acids: A New Class of Specific LTA4 Hydrolase Inhibitors", J. Med. Chem., 35, 1992, 3156-3169.

Martin, Y. C. et al., "Do Structurally Similar Molecules Have Similar Biological Activity?", J. Med. Chem., 45, 2002, 4350-4358.

Mitchell, R. H. et al., "The Neutral Deoxygenation (Reduction) of Aryl Carbonyl Compounds With Raney-Nickel. An Alternative to the Clemmenson, Wolf-Kishner or Mozingo (Thioketal) Reductions", Tetrahedron Letters, 21, 1980.

Penning, T. D. et al., "Structure-Activity Relationship Studies on 1-[2-(4-Phenylphenoxy)ethyl]pyrrolidine (SC-22716), a Potent Inhibitor of Leukotriene A4 (LTA4) Hydrolase", J. Med. Chem., 43(4), 2000, 721-735.

Pitt, W. R. et al., "Heteroaromatic Rings of the Future", J. Med. Chem., 52, 2009, 2952-2963.

Pozharskii, et al., Heterocycles in Life and Society Wiley, 1997, 1-6.

Rautio, J. et al., Nat. Rev. Drug Disc., vol. 7, 2008, 255-270.

Shen, H. C. et al., "A strategy of employing aminoheterocycles as amide mimics to identify novel, potent and bioavailable soluble epoxide hydrolase inhibitors", Bioorganic & Medicinal Chemistry Letters, 19, 2009, 5716-5721.

Shim, Y. M. et al., "Leukotriene A4 Hydrolase—An Evolving Therapeutic Target", Inflammatory Diseases-Immunopathology, Clinical and Pharmacological Bases, Dr Mahin Khatami (Ed.), InTech, 2012, 253-278.

Skerlj, R. et al., "Design and synthesis of pyridin-2-ylmethylaminopiperidin-1-ylbutyl amide CCR5 antagonists that are potent inhibitors of M-tropic (RS) HIV-1 replication", CA156: 10919, 2011.

(56) References Cited

OTHER PUBLICATIONS

Springman, E. B. et al., "A Phase 1 Study of Human Safety, Pharmacokinetics and Pharmacodynamics of CTX-4430", Pediatric Pulmonology, John Wiley, New York, NY, US, vol. 48, Oct. 1, 2013.
Vippagunta, S. R. et al., "Crystalline Solids", Advanced Drug Delivery Reviews, 48, 2001, 3-26.
Wolff, M. E. Burger's Medicinal Chemistry and Drug Discovery, Fifth Edition, vol. 5(1): Principles and Practice published by John Wiley and Sons, 1994, 975-977.

* cited by examiner

METHODS OF INHIBITING LEUKOTRIENE A4 HYDROLASE

RELATED APPLICATIONS

This application is a continuation of U.S. application Ser. No. 14/850,061, filed Sep. 10, 2015, which is a continuation of International Application No. PCT/US2014/023138, which designated the United States and was filed on Mar. 11, 2014, published in English, which claims the benefit of U.S. Provisional Application No. 61/776,981, filed on Mar. 12, 2013. The entire teachings of the above applications are incorporated herein by reference.

BACKGROUND OF THE INVENTION $LTA_4$-h is a monomeric, soluble 69 kD zinc metalloenzyme. It catalyses two reactions: the stereospecific epoxide hydrolase reaction to convert $LTA_4$ to leukotriene $B_4$ ($LTB_4$) and a peptidase cleavage of chromogenic substrates. Leukotriene $B_4$ ($LTB_4$) is a major pro-inflammatory mediator. $LTA_4$-h and receptors to $LTB_4$ are known to be elevated in a number of human lung diseases including cystic fibrosis, asthma and chronic obstructive pulmonary disease (COPD). Additionally, elevated levels of $LTA_4$-H have been located at active demyelinating lesions in the brains of patients with multiple sclerosis (MS).

$LTA_4$-h inhibitors have been described, for example, in U.S. Pat. No. 7,737,145 and U.S. Patent Application Publication No. 20100210630A1, the contents of each of which are incorporated by reference herein. A specific $LTA_4$-h inhibitor described in these patent publications is 4-{[(1S,4S)-5-({4-[4-oxazol-2-yl-phenoxy]phenyl}methyl)-2,5-diazabicyclo[2.2.1]heptan-2-yl]methyl}benzoic acid. In preclinical studies, this compound was shown to reduce the progression of chronic inflammation in several animal models. 4-{[(1S,4S)-5-({4-[4-oxazol-2-yl-phenoxy]phenyl}methyl)-2,5-diazabicyclo[2.2.1]heptan-2-yl]methyl}benzoic acid is in development for the treatment of specific inflammatory disorders.

It would be advantageous to develop additional methods of inhibiting $LTA_4$-h in human patients.

SUMMARY OF THE INVENTION

The present invention is directed to methods of inhibiting $LTA_4$-h in a human patient and methods of treating a condition ameliorated by the inhibition of leukotriene $A_4$ hydrolase activity in a human patient comprising administering to said human patient the compound, wherein the compound is 4-{[(1S,4S)-5-({4-[4-oxazol-2-yl-phenoxy]phenyl}methyl)-2,5-diazabicyclo[2.2.1]heptan-2-yl]methyl}benzoic acid, at a dose of about 100 mg or less, and wherein the compound is administered orally. In some embodiments, the compound is administered at a dose between about 1 mg and about 100 mg, a dose between about 1 mg and about 75 mg, a dose between about 1 mg and about 50 mg, a dose between about 1 mg and about 30 mg, or a dose between about 5 mg and about 25 mg. In some embodiments, the compound is administered at a dose between about 5 mg and about 15 mg. In certain aspects, the compound is administered at a dose of about 5 mg.

The invention also encompasses a pharmaceutical composition comprising the compound, 4-{[(1S,4S)-5-({4-[4-oxazol-2-yl-phenoxy]phenyl}methyl)-2,5-diazabicyclo[2.2.1]heptan-2-yl]methyl}benzoic acid, wherein the amount of the compound present in the composition is about 100 mg or less, and wherein the composition is an oral dosage form. In some embodiments, the amount of the compound is between about 1 mg and about 100 mg, between about 1 mg and about 75 mg, between about 1 mg and about 50 mg, between about 1 mg and about 30 mg, or between about 5 mg and about 25 mg. In some embodiments, the compound is present in the composition in an amount between about 5 mg and about 15 mg. In yet additional embodiments, the compound is present in the composition in an amount of about 5 mg.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
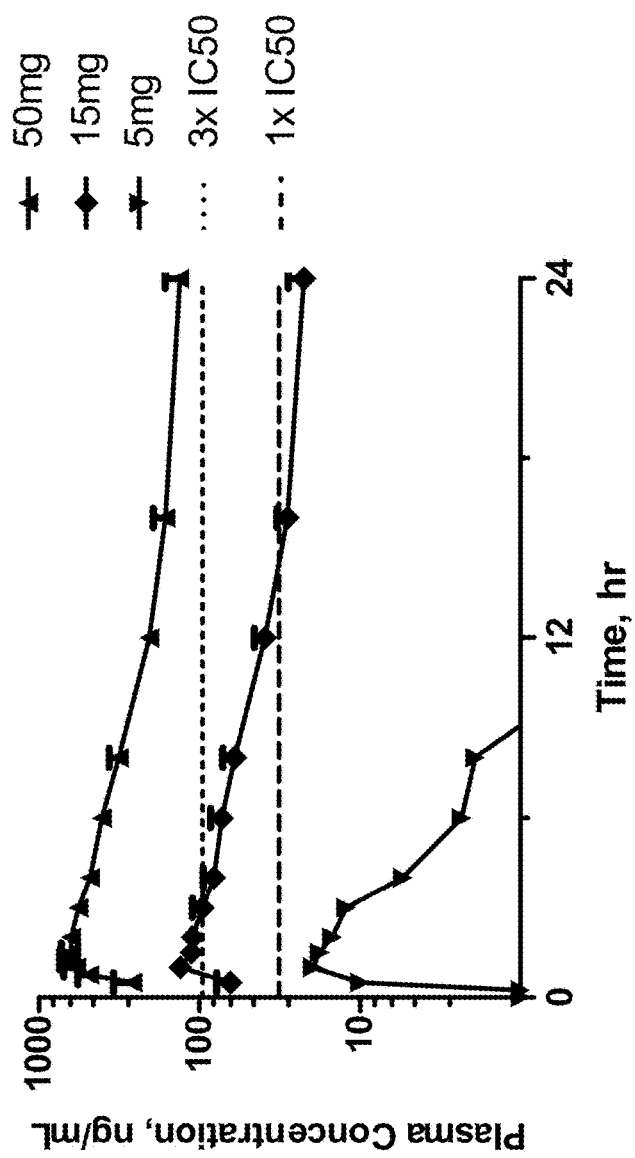
FIG. 1 shows a plot of plasma concentration (ng/ml) over time (hours) of 50 mg, 15 mg and 5 mg of 4-{[(1S,4S)-5-({4-[4-oxazol-2-yl-phenoxy]phenyl}methyl)-2,5-diazabicyclo[2.2.1]heptan-2-yl]methyl}benzoic acid. The two sets of dashed, horizontal lines indicate the plasma concentration that is three-times (3×) the $IC_{50}$ and the plasma concentration that is one-time (1×) the $IC_{50}$ of 4-{[(1S,4S)-5-({4-[4-oxazol-2-yl-phenoxy]phenyl}methyl)-2,5-diazabicyclo[2.2.1]heptan-2-yl]methyl}benzoic acid in human blood.

A description of preferred embodiments of the invention follows.

As used herein, the words "a" and "an" are meant to include one or more unless otherwise specified. For example, the term "an additional therapeutic agent" encompasses both a single additional therapeutic agent and a combination of two or more additional therapeutic agents.

It is to be understood that when the range of the dose or amount of the compound is described as "between" a low end of the range and "between" a high end of the range, the range is meant to include both, the low end and the high end as well as doses in between the low and high ends. For example, for "a dose between about 1 mg and about 100 mg," it is to be understood that the range includes the low end of the range, 1 mg, and the high end of the range, 100 mg, as well as the doses in between.

The present invention is based on the discovery that a low dose oral formulation of 4-{[(1S,4S)-5-({4-[4-oxazol-2-yl-phenoxy]phenyl}methyl)-2,5-diazabicyclo[2.2.1]heptan-2-yl]methyl}benzoic acid is therapeutically effective. Preclinical research conducted in mouse, rat, and dog models projected an effective oral dose of the compound for humans of at least 100 to 200 mg. However, pharmacokinetic studies (the results of which are described in more detail below) have demonstrated that an oral formulation containing less than 100 mg is effective. These studies have shown that a dose as low as 5 mg can achieve therapeutic levels of the compound in the blood.

The invention is directed to the administration of an effective oral dose of 4-{[(1S,4S)-5-({4-[4-oxazol-2-yl-phenoxy]phenyl}methyl)-2,5-diazabicyclo[2.2.1]heptan-2-yl]methyl}benzoic acid. This compound and methods for the preparation thereof have been described in detail in U.S. Pat. No. 7,737,145 and U.S. Patent Application Publication No. 20100210630A1, the contents of each of which are incorporated by reference herein 4-{[(1S,4S)-5-({4-[4-oxazol-2-yl-phenoxy]phenyl}methyl)-2,5-diazabicyclo[2.2.1]heptan-2-yl]methyl}benzoic acid has the chemical structure shown below:

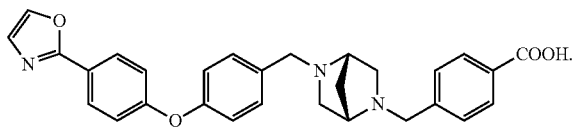 [SMILES: O=C(O)c1ccc(CN2C[C@@H]3C[C@H]2CN3Cc2ccc(Oc3ccc(-c4ncco4)cc3)cc2)cc1]

The methods of the invention relate to inhibiting $LTA_4$ hydrolase activity in human patients, and thus are useful in treating conditions which are ameliorated by the inhibition of $LTA_4$ hydrolase activity. Such diseases and conditions include inflammatory conditions and autoimmune diseases. Exemplary inflammatory conditions are pulmonary and respiratory tract inflammation.

In some embodiments, the condition that is treated is a chronic condition. Exemplary chronic conditions are cystic fibrosis, idiopathic pulmonary fibrosis, multiple sclerosis, inflammatory bowel disease, and interstitial lung disease associated with systemic sclerosis (scleroderma). In additional embodiments, the condition that is treated is an acute condition. Exemplary acute conditions are allergic rhinitis and myocardial infarction. The invention can also be used in the treatment of mild, non-life threatening conditions such as acne and gingivitis.

In some embodiments, the human patient is a pediatric patient. A pediatric patient can, for example, be a patient less than 16 years of age, less than 12 years of age, less than 10 years of age, less than 8 years of age, less than 6 years of age, less than 5 years of age, less than 2 years of age, or an infant. In some embodiments, the pediatric patient is suffering from cancer. In certain additional embodiments, the pediatric patient is suffering from a respiratory or pulmonary inflammation.

Conditions that can be ameliorated by $LTA_4$-h inhibition and that can be treated according to the methods of the invention include, for example, acute or chronic inflammation, anaphylactic reactions, allergic reactions, allergic contact dermatitis, allergic rhinitis, chemical and non-specific irritant contact dermatitis, urticaria, atopic dermatitis, psoriasis, fistulas associated with Crohn's disease, pouchitis, septic or endotoxic shock, hemorrhagic shock, shock-like syndromes, capillary leak syndromes induced by immunotherapy of cancer, acute respiratory distress syndrome, cystic fibrosis, traumatic shock, immune- and pathogen-induced pneumonias, immune complex-mediated pulmonary injury and chronic obstructive pulmonary disease, inflammatory bowel diseases (including ulcerative colitis, Crohn's disease and post-surgical trauma), gastrointestinal ulcers, diseases associated with ischemia-reperfusion injury (including acute myocardial ischemia and infarction, acute renal failure, ischemic bowel disease and acute hemorrhagic or ischemic stroke), immune-complex-mediated glomerulonephritis, autoimmune diseases (including insulin-dependent diabetes mellitus, multiple sclerosis, rheumatoid arthritis, osteoarthritis and systemic lupus erythematosus), acute and chronic organ transplant rejection, transplant arteriosclerosis and fibrosis, cardiovascular disorders (including hypertension, atherosclerosis, aneurysm, critical leg ischemia, peripheral arterial occlusive disease and Reynaud's syndrome), complications of diabetes (including diabetic nephropathy, neuropathy and retinopathy), ocular disorders (including macular degeneration and glaucoma), neurodegenerative disorders (including delayed neurodegeneration in stroke, Alzheimer's disease, Parkinson's disease, encephalitis and HIV dementia), inflammatory and neuropathic pain including arthritic pain, periodontal disease including gingivitis, ear infections, migraine, benign prostatic hyperplasia, and cancers (including, but not limited to, leukemias and lymphomas, prostate cancer, breast cancer, lung cancer, malignant melanoma, renal carcinoma, head and neck tumors and colorectal cancer).

The methods of the invention also encompass treating folliculitis induced by inhibitors of epidermal growth factor (EGF) or epidermal growth factor receptor (EGFR) kinase used in the treatment of solid tumors. Clinical trials have shown that folliculitis (inflammation of the hair follicle manifested by severe acne-like skin rash on the face, chest and upper back) is a major dose-limiting side effect of such treatments. Such folliculitis is associated with an infiltration of neutrophils suggesting products secreted by activated neutrophils to be the cause of the inflammation. The methods described herein can be used to inhibit neutrophil or eosinophil-mediated inflammation, and therefore encompass the treatment of folliculitis, thereby improving the quality of life of the treated cancer patients but also allowing for the increase of the dosage of the EGF inhibitor or EGFR kinase inhibitor or the extension of the duration of the treatment, resulting in improved efficacy of the desired inhibitor.

The methods also encompass the treatment of pulmonary and respiratory inflammation disorders in humans, including, but not limited to, asthma, chronic bronchitis, bronchiolitis, bronchiolitis obliterans (including such with organizing pneumonia), allergic inflammation of the respiratory tract (including rhinitis and sinusitis), eosinophilic granuloma, pneumonias, pulmonary fibroses, pulmonary manifestations of connective tissue diseases, acute or chronic lung injury, chronic obstructive pulmonary disease (COPD), adult respiratory distress syndrome (ARDS), and non-infectious inflammatory disorders of the lung characterized by eosinophil infiltration. In specific examples, the inflammation is eosinophil-mediated inflammation of the lung or tissues; neutrophil-mediated inflammation of the lung; lymphocyte-mediated inflammation of the lung; airway hyperresponsiveness; and airway and vascular inflammation.

The methods also encompass the treatment of myocardial infarction or susceptibility to myocardial infarction in humans, transient ischemic attack, transient monocular blindness, stroke or susceptibility of stroke, claudication, peripheral arterial occlusive disease or susceptibility to peripheral arterial occlusive disease, and acute coronary syndrome (such as unstable angina, non-ST-elevation myocardial infarction or ST-elevation myocardial infarction). The methods also encompass methods for reducing the risk of myocardial infarction, stroke or peripheral arterial occlusive disease in mammals and reducing the risk of a second myocardial infarction or stroke.

Also encompassed is the treatment of atherosclerosis in humans who require treatment (such as angioplasty, stents, coronary artery bypass graft) in order to restore blood flow in the arteries (such as in the coronary arteries).

The methods described herein can also be used in the treatment of neurodegenerative diseases. Non-limiting examples of neurodegenerative diseases that can be treated according to a method of the invention are amyotrophic lateral sclerosis (ALS), Parkinson's disease and Huntington's disease.

The methods also encompass the treatment of cancer. In some embodiments, the cancer is leukemia. Specific exemplary leukemias that can be treated by administering a compound of the invention are Chronic Granulocytic Leukemias, Chronic B-Cell Leukemias and Chronic Myelogenous Leukemias. The invention also encompasses a method of treating a solid tumor in a subject in need thereof. Non-limiting examples of solid tumors that can be treated according to the methods described herein are ovarian, esophageal and hepatocellular tumors.

In some embodiments, the invention is directed to a method of treating a condition selected from the group consisting of cystic fibrosis, idiopathic pulmonary fibrosis, interstitial lung disease associated with systemic sclerosis, atherosclerosis, osteoarthritis, Alzheimer's disease, osteoporosis, and type II diabetes, allergic rhinitis, acne, and gingivitis.

Also encompassed is a method of treating an eosinophilic disorder. Exemplary eosinophilic disorders are eosinophilic esophagitis, eosinophilic gastroenteritis, eosinophilic colitis, eosinophilic fasciitis, eosinophilic pneumonia, eosinophilic cystitis, hypereosinophilic syndrome and Churg Strauss Syndrome. In some embodiments, the eosinophilic disorder is eosinophilic esophagitis.

The invention encompasses methods wherein 4-{5-[4-(4-Oxazol-2-yl-phenoxy)-benzyl]-2,5-diaza-bicyclo[2.2.1]hept-2-ylmethyl}-benzoic acid is co-administered with at least one additional therapeutic agent. For example, in some embodiments, the condition is cancer and 4-{5-[4-(4-Oxazol-2-yl-phenoxy)-benzyl]-2,5-diaza-bicyclo[2.2.1]hept-2-ylmethyl}-benzoic acid is administered with a chemotherapeutic agent. In another example, the human patient is suffering from chronic obstructive pulmonary disease (COPD) and the additional therapeutic agent is a drug used in the treatment of COPD, such as a bronchodilator. In an additional example, the condition is COPD and the at least one additional therapeutic agent is selected from the group consisting of a beta-agonist, an anticholinergic, a glucocorticoid, or a combination thereof. In yet additional embodiments, the human patient is suffering from cystic fibrosis and the additional therapeutic agent is a drug used in the treatment of cystic fibrosis, for example, an antibiotic, a mucolytic, a surfactant, a pancreatic enzyme replacement drug, or a combination thereof. In yet other aspects of the invention, the condition is interstitial lung disease (ILD), a frequent complication of systemic sclerosis, and the additional therapeutic agent is a therapeutic agent used in the treatment of interstitial lung disease including, for example, glucocorticoids, cyclophosphamide, azathioprine, methotrexate, and mycophenolate mofetil. In some embodiments, the condition is multiple sclerosis and the additional therapeutic agent is a therapeutic agent used in the treatment of multiple sclerosis including, for example, teriflunomide (sold under the tradename AUBAGIO®), interferon-beta-1a (sold under the tradenames AVONEX® and REBIF®), interferon-beta-1b (sold under the tradenames BETASERON® and EXTAVIA®), glatiramer acetate (sold under the tradename COPAXONE®), fingolimod (sold under the tradename GILENYA®), mitoxantrone (sold under the tradename (NOVANTRONE®), and natalizumab (sold under the tradename TYSABRI®).

In some embodiments, 4-{5-[4-(4-Oxazol-2-yl-phenoxy)-benzyl]-2,5-diaza-bicyclo[2.2.1]hept-2-ylmethyl}-benzoic acid is co-administered with a beta-agonist. Exemplary beta-agonists are salbutamol, levalbuterol, formoterol, fenoterol, salmeterol, bambuterol, brocaterol, clenbuterol, terbutalin, tulobuterol, epinephrin, isoprenalin, and hexoprenalin. In another embodiment, the compound is co-administered with an anticholinergic agent. Exemplary anticholinergics are tiotropium, oxitropium, ipratropium, and glcopyrrolate. In a further embodiment, the compound is co-administered with a mucolytic and/or a surfactant. Exemplary mucolytics and surfactants are acetylcystein, ambroxol, carbocystein, tyloxapol, dipalmytoylphosphatidylcholin, recombinant surfactant proteins, and DNase. In one embodiment, the compound is co-administered with an antibiotic agent. Exemplary antibiotics are beta-lactam antibiotics, including amoxycillin, piperacillin, clavulan acid, and sulbactam, cephalosporines, including cefaclor, cefazedon, Cefuroxim, Cefoxitin, cefodizim, cefsulodin, cefpodixim, and cefixim, carbapenemes such as imipenem and cilastatin, monbactames, such as, aztrenonam, aminoglycosides, including streptomycin, neomycin, paromomycin, kanamycin, gentamycin, amicacin, tobramycin, and spectinomycine, tetracyclines, such as doxycyclin and minocycline, macrolides including erythromycine, clarithromycine, roxithromycine, azithromycine, josamycine, and spiramycine, gyrase inhibitors or quinolones such as ciprofloxacin, ofloxacine, levofloxacine, pefloxacine, lomefloxacine, fleroxacine, clinafloxacine, sitafloxacine, gemifloxacine, balofloxacine, trovafloxacine, and moxifloxacine, sulfonamides and nitroimidazoles including metronidazol, tinidazol), chloramphenicol, lincomycine, clindamycine, and fosfomycine, and glycopeptides such as Vancomycine and Teicoplanine. In yet additional embodiments, the compound is co-administered with an anti-inflammatory drug. Exemplary anti-inflammatory drugs include romoglycate and nedocromil. In an additional aspect, the compound is co-administered with a corticosteroid. Exemplary corticosteroids are beclomethasone, betamethasone, budesonide, ciclesonide, flunisolide, fluticasone, icomethasone, mometasone, rofleponide, triamcinolone, bradykinine, prostaglandine, leucotriene and platelet activating factor antagonists.

It is to be understood that when a compound is co-administered with at least one additional therapeutic agent, the compound can be administered simultaneously with, prior to, or after administration of one or more other therapeutic agents. Such combination therapy includes administration of a single pharmaceutical dosage formulation which contains the compound and one or more additional active agents, as well as administration of the compound and each active agent in its own separate pharmaceutical dosage formulation. For example, the compound and the other therapeutic agent can be administered to the patient together in a single oral dosage composition such as a tablet or capsule, or each agent can be administered in separate oral dosage formulations. Where separate dosage formulations are used, the compound and one or more additional active agents can be administered at essentially the same time, i.e., concurrently, or at separately staggered times, i.e., sequentially; and/or in the same treatment session and/or as part of the same treatment regimen; combination therapy is understood to include all these regimens.

The invention also encompasses pharmaceutical compositions. The pharmaceutical compositions of the invention can be prepared by combining 4-{[(1S,4S)-5-({4-[4-oxazol-2-yl-phenoxy]phenyl}methyl)-2,5-diazabicyclo[2.2.1]heptan-2-yl]methyl}benzoic acid with an appropriate pharmaceutically acceptable carrier, diluent or excipient, and can be formulated into preparations in solid, semi-solid, or liquid forms, such as tablets, capsules, powders, granules, solutions, and the like. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet can be a single dosage unit or a tablet can be one-half of single dosage unity. Actual methods of preparing such dosage forms are known, or will be apparent, to those skilled in this art; for example, see The Science and Practice of Pharmacy, 20th Edition (Philadelphia College of Pharmacy and Science, 2000) and Remington: The Science and Practice of Pharmacy, 22nd Edition (Pharmaceutical Press and Philadelphia College of Pharmacy at University of the Sciences, 2012). The composition to be administered will, in any event, contain an effective amount of a compound as described herein (for example, 100 mg or less), or a pharmaceutically acceptable salt thereof, for treatment of a disease or condition of interest in accordance with the teachings of this invention.

A pharmaceutical composition of the invention can be in the form of a solid or liquid. In one aspect, the carrier(s) are particulate, so that the compositions are, for example, in tablet or powder form. The carrier(s) can be liquid, with the compositions being, for example, an oral syrup. Thus, the pharmaceutical composition can be in either solid or liquid form, where semi-solid, semi-liquid, suspension and gel forms are included within the forms considered herein as either solid or liquid. As a solid composition for oral administration, the pharmaceutical composition can be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example a gelatin capsule, it may contain, in addition to materials of the above type, a liquid carrier such as polyethylene glycol or oil.

The pharmaceutical composition can be in the form of a liquid, for example, an elixir, syrup, solution, emulsion or suspension. The composition can contain, in addition to combining 4-{[(1S,4S)-5-({4-[4-oxazol-2-yl-phenoxy]phenyl}methyl)-2,5-diazabicyclo[2.2.1]heptan-2-yl]methyl}benzoic acid, one or more of a sweetening agent, preservatives, dye/colorant and flavor enhancer. The liquid pharmaceutical compositions of the invention, whether solutions, suspensions or other like form, can include one or more of the following adjuvants: sterile diluents, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose.

The pharmaceutical composition of the invention can include various materials, which modify the physical form of a solid or liquid dosage unit. For example, the composition can include materials that form a coating shell around the active ingredients. The materials that form the coating shell are typically inert, and may be selected from, for example, sugar, shellac, and other enteric coating agents. Alternatively, the active ingredients can be encased in a gelatin capsule.

In certain aspects of the invention, the compound, 4-{[(1S,4S)-5-({4-[4-oxazol-2-yl-phenoxy]phenyl}methyl)-2,5-diazabicyclo[2.2.1]heptan-2-yl]methyl}benzoic acid, is a milled solid. In some aspects, the milled solid has a monodisperse particle size distribution having a D90 of about 50 microns or less. In some embodiments, the milled solid has a monodisperse particle size distribution having a D90 of about 15 microns or less. In yet another embodiment, the milled solid has a monodisperse particle size distribution having a D90 between 10 and 15 microns. D90 refers to a particle size where 90 volume percent of the particles are smaller than the indicated diameter.

Figure 2:
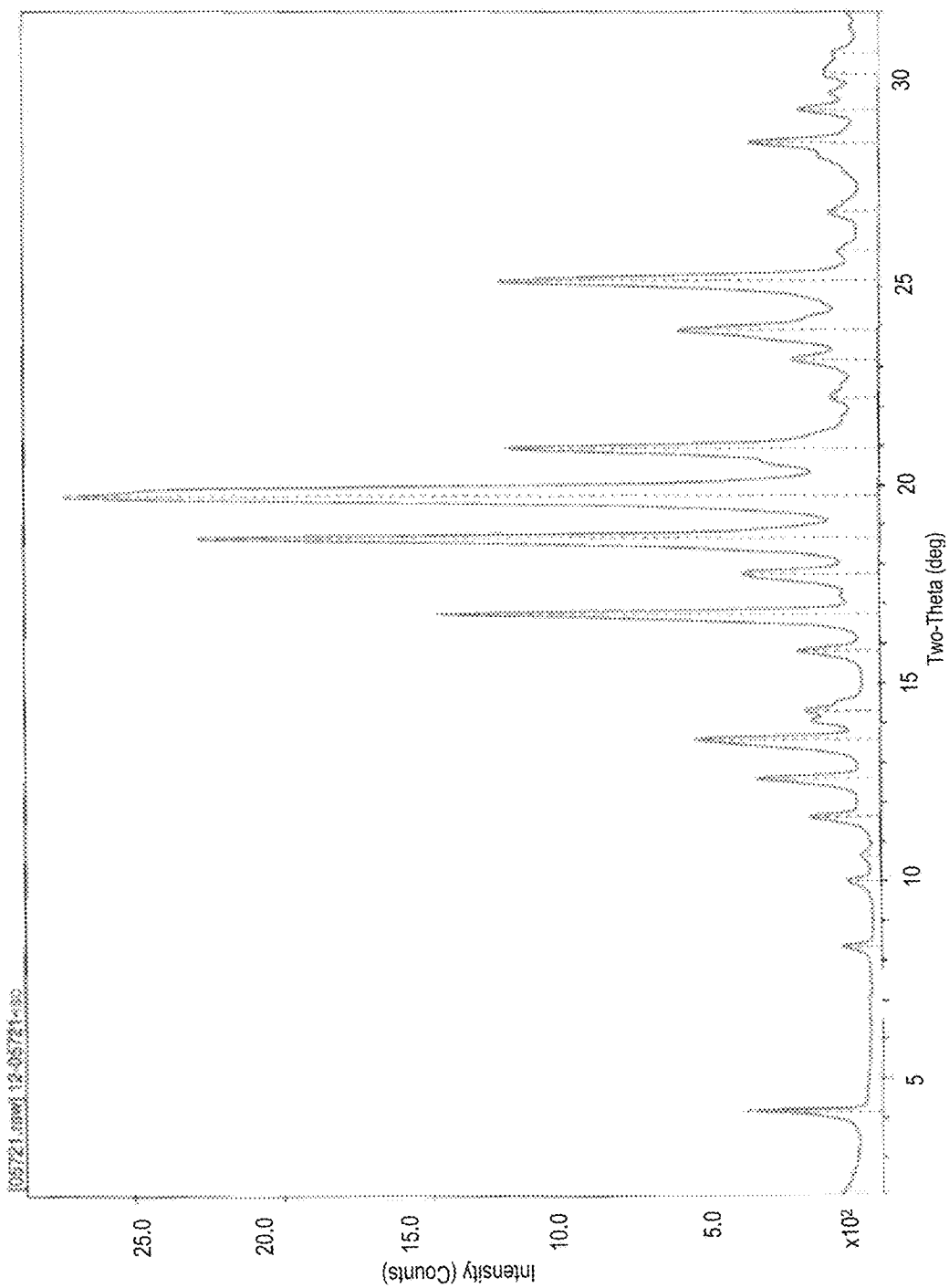
FIG. 2 shows the x-ray powder diffraction pattern of 4-{[(1S,4S)-5-({4-[4-oxazol-2-yl-phenoxy]phenyl}methyl)-2,5-diazabicyclo[2.2.1]heptan-2-yl]methyl}benzoic acid.

In some embodiments, the compound is a solid that is amorphous or crystalline in physical structure. In certain aspects, the compound is a solid that is crystalline. In yet additional embodiments, the compound is crystalline, wherein the crystalline form is characterized by the x-ray powder diffraction pattern substantially as shown in FIG. 2. In this context, the term "substantially" refers variations in intensity and 2-theta values typically observed in the art depending on instrument and sample preparation.

In certain embodiments, the compound, 4-{[(1S,4S)-5-({4-[4-oxazol-2-yl-phenoxy]phenyl}methyl)-2,5-diazabicyclo[2.2.1]heptan-2-yl]methyl}benzoic acid is a powder. In certain additional aspects, the pharmaceutical composition comprises the compound as a powder and an excipient selected from the group consisting of a carrier, an emulsifier, a disintegrants, a lubricant, a glidants or flow aid, or a combination of any thereof. Non-limiting examples of carriers are mannitol and lactose. A non-limiting example of an emulsifier is methylcellulose. Non-limiting examples of disintegrants are croscarmellose or crospovidone. A non-limiting example of a lubricant is magnesium stearate. A non-limiting example of a glidant or flow aid is silicon dioxide. In certain embodiments, the pharmaceutical composition comprises the compound as a solid powder and the composition further comprises lactose, methylcellulose, crospovidone, and magnesium stearate. In yet additional embodiments, the pharmaceutical composition comprises the compound as a solid powder and the composition further comprises mannitol, methylcellulose, croscarmellose and/or magnesium stearate. In additional aspects, the pharmaceutical composition comprises the compound as a solid powder and the composition further comprises lactose, methylcellulose, crospovidone, and/or magnesium stearate and further comprises a glidant or flow aid. In yet additional embodiments, the pharmaceutical composition comprises the compound as a solid powder and the composition further comprises mannitol, methylcellulose, croscarmellose and/or magnesium stearate, and further comprises a glidants of flow aid. In some embodiments, the glidants or flow aid is silicon dioxide.

In some embodiments, the pharmaceutical composition comprises the compound as a solid powder or powder blend and wherein the pharmaceutical composition is in the form of a capsule or a tablet. In an additional embodiment, the pharmaceutical composition is capsule containing the compound as a solid powder or powder blend. In yet another embodiment, the pharmaceutical composition is a gelatin capsule containing compound as a solid powder or powder blend.

The invention is illustrated by the following non-limiting examples.

EXEMPLIFICATION

Example 1

The $IC_{50}$ of 4-{[(1S,4S)-5-({4-[4-oxazol-2-yl-phenoxy]phenyl}methyl)-2,5-diazabicyclo[2.2.1]heptan-2-yl]methyl}benzoic acid in human whole blood has been determined using an ex vivo assay. The human whole blood assay has been described in Penning et al (2000), Structure and Activity Relationship Studies on 1-[2-(4-Phenylphenoxy)ethyl]pyrrolidone (SC-22716), a Potent Inhibitor of Leukotriene A4 (LTA4) hydrolase, *J. Med. Chem.* 43: 721-735, the contents of which are expressly incorporated by reference herein. In this assay, LTB4 production is stimulated by addition of calcium ionophone (A23187) in the absence or presence of varied concentrations of 4-{[(1S,4S)-5-({4-[4-oxazol-2-yl-phenoxy]phenyl}methyl)-2,5-diazabicyclo[2.2.1]heptan-2-yl]methyl}benzoic acid. The ability of 4-{[(1S,4S)-5-({4-[4-oxazol-2-yl-phenoxy]phenyl}methyl)-2,5-diazabicyclo[2.2.1]heptan-2-yl]methyl}benzoic acid to reduce is LTB4 production is determined by ELISA. This ELISA assay was performed using the Leukotriene B4 EIA Kit available from Cayman Chemical (Item No. 520111) and the assay was performed according to the manufacturer's instructions.

In this assay, 4-{[(1S,4S)-5-({4-[4-oxazol-2-yl-phenoxy]phenyl}methyl)-2,5-diazabicyclo[2.2.1]heptan-2-yl]methyl}benzoic acid has an $IC_{50}$ in human whole blood of approximately 30 ng/mL (60 and 68 nanomolar in male and female blood, respectively). The results of this assay are shown in FIG. 1. Human pharmacokinetics demonstrate that a 15 mg dose achieves a blood plasma level that exceeds the $IC_{50}$ for over 12 hours and 50 mg exceeds by 3-times the $IC_{50}$ for over 24 hours, while 5 mg nearly achieves the $IC_{50}$ at its peak concentration. Thus, oral human doses as low as 10 mg can provide therapeutic benefit in the current formulation and, with improved formulation, doses as low as 5 mg can achieve therapeutic levels of the compound in blood.

While this invention has been particularly shown and described with references to preferred embodiments thereof, it will be understood by those skilled in the art that various changes in form and details may be made therein without departing from the scope of the invention encompassed by the appended claims.

What is claimed:

1. A method for the treatment of chronic obstructive pulmonary disease in a human patient in need thereof comprising administering to said human patient the compound, 4-{[(1S,4S)-5-({4-[4-oxazol-2-yl-phenoxy]phenyl}methyl)-2,5-diazabicyclo[2.2.1]heptan-2-yl]methyl}benzoic acid, at a dose of about 50 mg or less, and wherein the compound is administered orally, wherein the dose achieves a blood plasma level that exceeds or achieves the $IC_{50}$ of the compound for at least 12 hours, and wherein the $IC_{50}$ is that for leukotriene A4 hydrolase activity inhibition.

2. The method of claim 1, wherein the compound is administered at a dose between about 1 mg and about 50 mg.

3. The method of claim 2, wherein the compound is administered at a dose between about 1 mg and about 30 mg.

4. The method of claim 1, wherein the human patient is a pediatric patient.

5. The method of claim 1, wherein the compound is co-administered with at least one additional therapeutic agent.

6. The method of claim 5, wherein the at least one additional therapeutic agent is a bronchodilator.

7. The method of claim 5, wherein the additional therapeutic agent is selected from the group consisting of a beta-agonist, an anticholinergic, a glucocorticoid, or a combination thereof.

8. The method of claim 1, wherein the dose achieves a blood plasma level that exceeds the $IC_{50}$ of the compound for at least 24 hours.

* * * * *